United States Patent [19]
Smith

[11] Patent Number: 5,377,670
[45] Date of Patent: Jan. 3, 1995

[54] INSULATED BREATHING TUBE

[76] Inventor: Charles A. Smith, 811 Starlite Dr., Louisville, Ky. 40207

[21] Appl. No.: 900,995

[22] Filed: Jun. 19, 1992

Related U.S. Application Data

[63] Continuation-in-part of Ser. No. 593,555, Oct. 9, 1990, abandoned, which is a continuation-in-part of Ser. No. 275,940, Nov. 25, 1988, abandoned, which is a continuation-in-part of Ser. No. 19,248, Feb. 26, 1987, abandoned, which is a continuation-in-part of Ser. No. 910,625, Sep. 23, 1986, abandoned.

[51] Int. Cl.$^6$ .............. A61M 16/00; A61M 5/32; A62B 7/00; F24J 3/00

[52] U.S. Cl. .............. 128/204.17; 128/911; 128/912; 128/207.14; 604/163; 604/171; 138/122

[58] Field of Search ......... 128/200.24, 204.15–204.18, 128/205.12, 911, 912, 207.14; 138/114, 118.1, 122; 285/45, 47, 53, 417, 419; 604/163, 171, 197, 198

[56] References Cited

U.S. PATENT DOCUMENTS

| | | | |
|---|---|---|---|
| 3,383,875 | 5/1968 | Haas | 138/122 |
| 3,490,496 | 1/1970 | Stearns | 138/112 |
| 3,814,091 | 6/1974 | Henkin | 128/202.22 |
| 4,013,122 | 3/1977 | Long | 128/204.17 |
| 4,232,667 | 11/1980 | Chalon et al. | 128/204.17 |
| 4,281,652 | 8/1981 | Miller | 128/204.25 |
| 4,320,754 | 3/1982 | Watson et al. | 128/205.13 |
| 4,415,389 | 11/1983 | Medford et al. | 138/122 |
| 4,423,283 | 12/1983 | Weismann | 138/122 |
| 4,463,755 | 8/1984 | Suzuki | 128/204.18 |
| 4,621,634 | 11/1986 | Nowacki et al. | 128/204.18 |
| 4,637,384 | 1/1987 | Schroeder | 128/204.18 |
| 4,838,258 | 6/1989 | Dryden et al. | 128/204.18 |
| 4,967,744 | 11/1990 | Chua | 128/204.18 |

FOREIGN PATENT DOCUMENTS

| | | | |
|---|---|---|---|
| 0706316 | 5/1941 | Germany | 128/204.18 |
| 2824799 | 12/1978 | Germany | 128/204.18 |

*Primary Examiner*—Kimberly L. Asher

[57] ABSTRACT

The present invention provides an insulated breathing tube arrangement to prevent heat loss from the inhalant gas in a recirculatory aided breathing circuit thereby reducing internal vapor condensation commonly associated with such breathing circuits while also stabilizing the relative temperature and humidity within such breathing circuits. The insulated breathing tube arrangement includes a thin flexible partially longitudinally compressed casing surrounding a thicker corrugated tube. The thin casing allows for hairpin bending of the breathing tube arrangement and provides an insulating dead air space around the corrugated tube. In another arrangement selected enlarged corrugations are provided in spaced relation along the corrugated tube to engage the inner surface of the casing in a preselected spaced arrangement with respect to said corrugated tube to compartmentalize insulating dead air spaces between the tube and the casing.

1 Claim, 4 Drawing Sheets

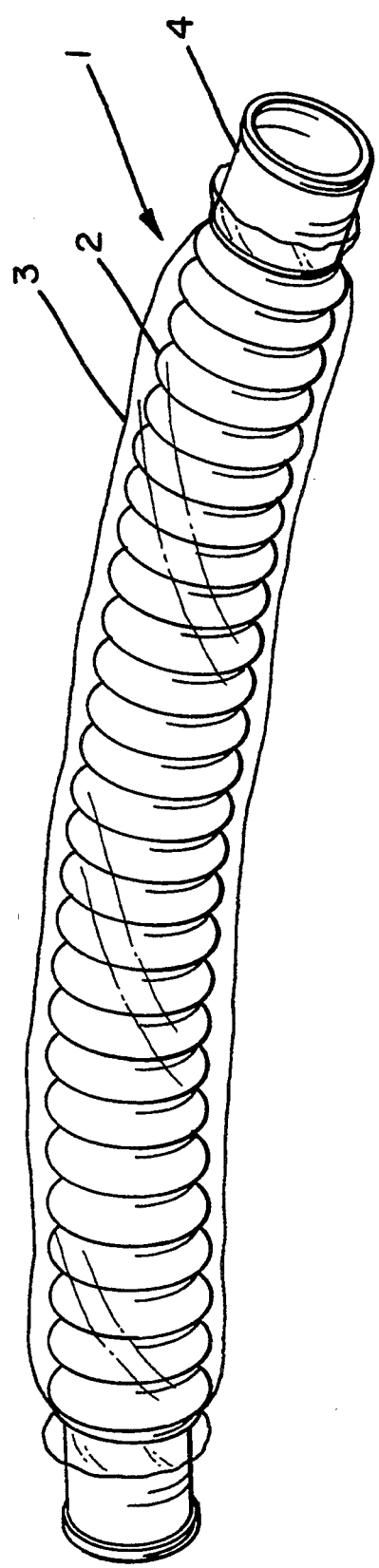
Fig. I

INSULATED BREATHING TUBE

This application is a continuation-in-part of U.S. Ser. No. 07/593,555 filed Oct. 9, 1990, now abandoned which was a continuation-in-part of U.S. Ser. No. 07/275,940 filed Nov. 25, 1988, now abandoned, which was a continuation-in-part of U.S. Ser. No. 07/019,248, filed Feb. 26, 1987, now abandoned, which was a continuation-in-part of U.S. Ser. No. 06/910,625, filed Sept. 23, 1986, now abandoned.

BACKGROUND OF THE INVENTION

The present invention relates to breathing tube comprising a corrugated tube and a casing for reduction of heat transfer from the corrugated tube commonly utilized with recirculatory aided breathing circuits, and the ambient atmosphere. Briefly, the invention includes a tubular sleeve or casing which encloses an air impervious conduit inside the casing in such a manner that a dead air space is created between the outside of the conduit and the inside of the casing. The linear volume of the dead air space is approximately equal to the linear volume of the conduit it encompasses.

Various type tubular and conduit arrangements are presently in use for the maintenance of respiration and conditioning of the air supply to a patient. Such circuits are commonly used for the introduction of anesthesia during surgery and/or attached to respirators and/or other types of patient ventilation/breathing devices. A complete respiratory system usually includes a pressure generator (mechanical or manually powered), inhalation tube, exhalation tube, "Y" piece, and a means of attaching the inhalation and exhalation tubes to the patient, (i.e. by endotracheal catheter, or face mask, etc). The respirator then mechanically controls the flow of gases within the circuit which may also include humidifying and/or temperature adjusting devices interconnected with the circuit.

The traditional circuit is attached to the patient's airway opening via a Y-shaped connector. The arms of this "Y" connector are attached to inhalation and exhalation tubes and the respirations of the patient are controlled by the operator/respirator, (i.e. number of respirations per minute, volume of each respiration, etc).

When artificial ventilation of a patient is required over extended periods of time the inhalant should have an inspiration temperature within the range of normal body temperature and a relative humidity approaching 100% in order to minimize damage to the patients airway, aveoli, bronchiles and other parts of the lungs.

Often, in association with the traditional circuit, a combination of temperature-humidity control devices may be employed on the inhalation side of the circuit to attempt to assure that the optimum temperature and humidity conditions are maintained.

A common problem associated with traditional circuits is the distance between the inhalant source and humidifier-temperature control device and the respiratory passageway of the patient ventilated is quite long. The long distance that the inhalants must travel through the conduits, both to and from the humidifier-temperature control device frequently allows the inhalants to fall below the optimal temperature and humidity levels for such inhalants entering the patient's lungs. Thus, prolonged exposure may damage the lungs and also may lower the patient's body temperature below desirable levels.

Attempts have been made to alleviate the aforenoted problem associated with a traditional circuit by placing temperature-humidifier control devices in close proximity to the patient. However, because the traditional ciruit is already cumbersome, the addition of such devices at this point on the inhalation circuit cause most attendants and patients to find this configuration greatly annoying and inconvenient, and potentially dangerous.

In an attempt to alleviate the cumbersomeness of a traditional circuit, British Patent Publication No. 2,029,703A, discloses the use of a single limb anesthesia circuit consisting of two corrugated wall tubes, where each tube is affixed at one end to a respirator and at the other to a connector to the patient's airway. Because both inhalation and exhalation tubes were affixed to a connector on the patient side, the inner tube offered resistance and restricted the outer tube when pressure within the inner tube was increased, i.e. as with every forced inhalation by the respirator.

The previously discussed deficiencies of British Patent Publication No. 2,029,703A were attempted to be rectified in U.S. Pat. No. 4,463,755, to Suzuki. Suzuki defines an inner inhalation tube coaxially circumscribed by an outer exhalation tube, the resistance between the two tubes was minimized by retaining members affixed to the inner tube at a fixed distance. However, there are two major problems associated with a Suzuki-type circuit. First, they are expensive and second, there may be a build-up of liquid condensation and other matter within the exhalation tube which is caused by the difference in the temperature gradient between the patient's exhalant breath and the atmospheric temperature in contact with the exhalant tube.

Further, this condensation provides an environment for germicidal growth when used for prolonged periods. This germicidal growth can be re-aspirated in the lungs of the patient increasing the possibility of complicating infections which increase morbitity and mortality. The aforenoted disadvantageous condensation is commonly associated with almost all traditional breathing circuits.

Another prior art U.S. Pat. No. 4,232,667 to Chalon, et. al., discloses a single limb breathing circuit used for anesthesia introduction. The Chalon invention defines a closed circuit system consisting of an absorber container that removes $CO_2$ from the circuit thereby permitting only Oxygen and anesthesia gasses to be continuously circulated within the system. The primary benefits disclosed in Chalon, et. al. are reduced anesthesia costs because the anesthesia unabsorbed by the lungs is recirculated to the patent. Thus, less anesthesia is needed for the operation and there is a lower probability of operating room explosions due to the absence of highly volatile anesthestic gasses being exhaled from the patient and released into the operating room. However, Chalon suffers from the same disadvantages as Suzuki.

U.S. Pat. No. 3,814,091 to Henkin teaches a breathing apparatus using a corrugated breathing tube with a flexible tubular enclosure surrounding a portion of the breathing tube but, contrary to the present invention where there is no air flow between the hose and the envelope, in Henkin flow conduits or holes are required in the breathing tube to allow air flow into the space between the breathing tube and the envelopes. Consequently, the area between the breathing tube and the tubular enclosure (envelope) of Henkin is not a dead air space, and therefore not insulating as it is in the present invention. In Henkin the outer tube enclosure acts like a balloon which when squeezed by the operator delivers a volume of air to the patient's air stream. Moreover in Henkin, the outer envelope may contain a slit to act as a pressure relief means.

U.S. Pat. No. 2,119,446 like U.S. Pat. No. 3,814,091 relates to a perforated corrugated tube which is surrounded by a balloon.

U.S. Pat. No. 4,269,193 teaches a breathing apparatus with concentric air flow tubes where air flows through the annular area so the area is not a dead air space as provided by the present invention. Moreover, the air flowing in the outer tube is subject to uninhibited cooling and condensation which is sought to be prevented by the present invention.

U.S. Pat. No. 4,300,547 teaches an inhalation conduit which is covered with a sheath of material which can be wetted with a liquid so the conduit is cooled by evaporation.

Likewise U.S. Pat. No. 3,924,619 teaches a heat exchange means not an insulating arrangement for breathing conduits.

U.S. Pat. No. 3,185,182 to Waddell relates to a conduit having a corrugated tubular body with a plastic coated circumferential reinforcement containing an additional reinforcement member. The tube does not have a dead air insulating space.

U.S. Pat. No. 3,490,496 to Stearns relates to flexible transfer lines for cryogenic liquids. The coaxial tubing has inner and outer concentrically arranged tubes and spacing means therebetween.

U.S. Pat. No. 2,898,941 to Kilcup provides an inhaler tube having exterior helical corrugations to import maximum flexibility while at the same time maintaining the tube free from kinking with the tube also having a smooth interior surface that readily lends itself to thorough cleansing and sterilization.

U.S. Pat. No. 3,858,615 to Weigl describes a kink-resistant hose construction of a one piece tube of flexible material having a smooth cylindrical inner wall surface for efficient air flow and easy cleaning and having axially spaced concentric rings on its outer wall.

U.S. Pat. No. 4,000,341 to Matson refers to a autoclavable corrugated respiratory air tubing which is translucent so that liquid build-up in the tubing can be seen through the walls of the tubing.

U.S. Pat. No. 2,073,335 to Connell is a breathing tube which employs various reinforcements which may be applied by hand or by suitable mechanical means.

U.S. Pat. No. 4,415,389 to Medford suggests an inner corrugated hose construction and a sleeve disposed around the hose having the function of improving the fluid pressure resistance and the external water resistance, the sleeve being taut and free of sags.

U.S. Pat. No. 4,007,737 to Paluch relates to a anesthesia breathing circuit having inner and outer tubes with spacer means for supporting and maintaining the tubes enspaced in relatively fixed spacial relation.

Also insulating ventilation hoses is suggested by Drs. Alan R. Mizutani, Ozahi, and Rusk in ANESTH ANALG. 1991,72:561-7.

SUMMARY OF THE INVENTION

Patients receiving artificial ventilation/medical attention over prolonged periods are usually in an air conditioned environment, cooler than their body temperature, both for their own comfort and the comfort of attending personnel. However, the air conditioned atmosphere also cools respiratory equipment used in such conditions and can cause undesirable liquid condensation in the systems.

Accordingly, the present invention provides a method and apparatus for reducing heat transfer in a recirculatory aided breathing circuit to stabilize the thermal gradient and therefore reduce heat losses between the inhalant gas and the surrounding atmosphere and reduce condensation commonly associated with such breathing circuits. Consequently, the relative humidity and temperature within such a breathing circuit are stabilized.

More specifically the invention includes an insulated breathing tube arrangement having an air impervious corrugated tube for carrying respiratory gasses and an outer casing of first internal diameter for insulating the corrugated tube said corrugated tube being located within said casing and having an outer diameter less than said internal diameter of said casing, said casing being of an overall length greater than the length of said corrugated tube and being sealed at its ends to the ends of the corrugated tube such that the casing is in a slightly longitudinally compressed state relative to said corrugated tube thereby defining an insulating dead air space between said corrugated tube and said casing, said casing further being of a thickness which is less than the thickness of said corrugated tube.

Within the scope of the present invention are features that are inexpensive, easily fabricated and highly effective to reduce condensation of vapor within a breathing circuit. Features within the scope of the present invention are particularly useful when utilized with corrugated hose of the type commonly used to carry gases to and from a patient during medical treatment or in a life sustaining practice.

Devices within the scope of the present invention facilitate the maintenance of adequate moisture conditions in the lungs of a patient who would otherwise be exposed to breathing the dry gasses of an artificial environment such as a person being treated or maintained by a mechanical breathing apparatus such as a ventilator or during an anesthesia/surgical procedure.

Moreover, the apparatus of the present invention assists in the maintenance of the normal body temperature of a patient in situations where the normal body temperature is desired since body heat loss may occur by breathing cool gasses present in a closed circuit.

Devices within the scope of the present invention reduce or totally eliminate problems occurring in anesthetize caused by "rainout", that is the condensation and accumulation of liquid inside the breathing hoses during use.

Devices within the scope of the present invention also maintain the flexibility of the commonly available air hoses and permit visual observation of any condensation which may occur.

Particularly, the present invention provides a method for preventing heat transfer to or from a recirculatory aided breathing circuit to stabilize the thermal gradient between the breathing circuit and the surrounding atmosphere to reduce internal vapor condensation commonly associated with such breathing circuits while also stabilizing the relative humidity within such breathing circuit.

In the preferred form a tubular casing or sleeve is provided to surround a corrugated tube of the circuit to provide insulating dead air space therebetween. In another arrangement selected corrugations are provided in spaced relation along the corrugated tube to engage the inner surface of the casing to define the dead air space.

While various arrangements within the scope of the present invention are disclosed herein and discussed hereinafter it will be understood that the arrangements are provided for purposes of illustration only and not by way of limitation and that various other arrangements also within the scope of the present invention will occur to those skilled in the art upon reading the disclosure set forth hereinafter.

BRIEF DESCRIPTION OF THE DRAWINGS

Examples within the scope of the present invention are illustrated in the accompanying drawings wherein.

FIG. 1 is a perspective view of a corrugated hose of the type useful within the scope of the present invention showing its encasement by a tubular casing to provide a combination within the scope of the present invention;

DETAILED DESCRIPTION OF THE DRAWINGS

Referring first to FIG. 1 a breathing tube 1 of the type contemplated by the present invention is illustrated where corrugated tube 2 of the type generally known in the art is provided. A casing 3 is provided, as described hereinafter, to encase the tube 2 to define an insulating dead air space between the breathing tube 2 and the casing 3. A tip 4 is provided at the end of the tube 2 to facilitate connection of the tube either to a source of gas or to a device to be received by a patient. As is known in the art a similar arrangement can be provided on the other end of the tube and the tube then is utilized to supply gasses from the source to the patient. As is also known in the art, the corrugations are provided along the length of the tube to facilitate bending or shaping the tube without risk of stopped gas flow because of kinking.

Figure 2:
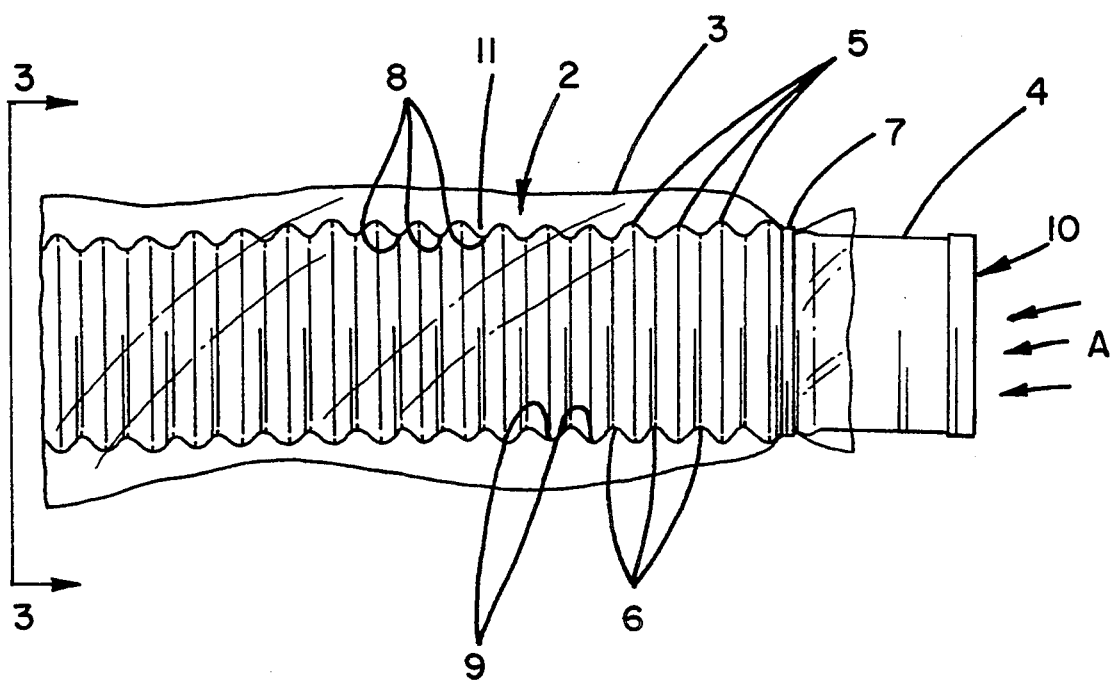
FIG. 2 is an enlarged view of a portion of an arrangement within the scope of the present invention.

FIG. 2 is a view, partially in cross section, of a tube of the type shown in FIG. 1 where the corrugation crests 5 and valleys 6 are shown as is the casing 3.

The casing 3 can be retained on the tube 2 by any convenient means and in the arrangements shown an elastomeric fastener, for example a rubberband 7, or "O" ring is provided to be placed over the outer surface of the casing 3 and received between the raised portions of the tubing to hold the casing under the rubberband 7 in one of the valleys between the corrugations.

While other fastening means can be provided the one illustrated in FIG. 2 has been found to be particularly effective and very inexpensive.

There are several features which should be considered in connection with the arrangement shown in FIG. 2, the first of which is that the air represented by the arrows A flows through the opening 10 in the tube and contacts principally the lower indented portions 8 of the corrugations.

As is known in the art the heat transfer occurring in the tube occurs in the area of highest Reynolds number. Since the Reynolds number is dependent on velocity the highest heat transfer will occur in the areas 8 on the inner surface of the corrugations through the indented portions 8 of the corrugations. Conversely, the air trapped in the depressions 9 is generally stagnate compared with the air flowing through opening 10. Since the stagnate air provides some insulation within the tube, less heat transfer occurs through the area 9 in the upstanding portions of the corrugations.

In practice, without the use of the casing 3, heat is transferred through the areas 8 of the corrugated tubing and convective currents flowing through areas 11 facilitate loss of heat through the indented portions 8 to the ambient air surrounding the tube 2.

In accordance with one feature of the present invention it is recognized that by use of the casing 3 these convective currents are prevented so the heat loss which would otherwise occur through the portions 8 of the corrugated tubing is substantially reduced. Further, the casing 3 should have a wall thickness less than the thickness of the corrugated tubing wall to maintain flexibility of the entire unit yet because of the lack of corrugations the casing substantially reduces the surface area available for convective heat transfer and additionally provides another barrier for radiant heat loss.

Casing 3 most preferably is clear, as is the corrugated tubing so that the presence of condensate in the tube can be monitored visually. Additionally, the overall length of the casing is less than the extended length of the corrugated tubing i.e. when the tubing 2 extended to the point that the sidewalls are no longer corrugated but rather are straight. Thus it can be seen that the surface of the casing is substantially less by approximately ½ than the surface area of the corrugated tubing to further reduce heat transfer.

Accordingly, the arrangement shown permits the transmission of a stream of air through a relatively long tube with virtually no change in temperature and with very little additional expense, bulk, or loss of flexibility or loss of visual contact with tube 2.

If any of the previously discussed devices are used to supply heat to the gasses within the tubing to prevent condensation and loss of temperature the features provided by the present invention would enhance the performance of such devices.

It is further recognized that the casing 3 is sized so that it does not contact corrugation crests 5 except on a random basis by gravity.

Figure 3:
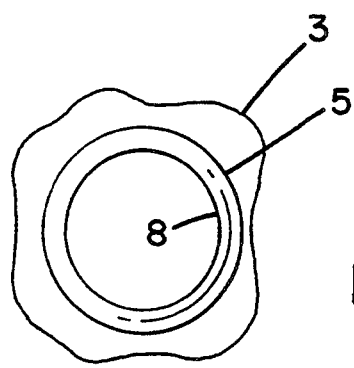
FIG. 3 is a cross sectional view taken along a plane passing through line 3—3 of FIG. 2.

FIG. 3 is a cross sectional view of the hose of FIG. 2 taken along line 3—3 thereof. The loose fitting nature of casing 3 is clearly evident in FIG. 3.

Moreover, various arrangements can be utilized within the scope of the present invention, for example spacers could be placed along the length of the corrugated tube 12 having a diameter equal to the diameter of intermittently spaced corrugations 2.

Figure 4:
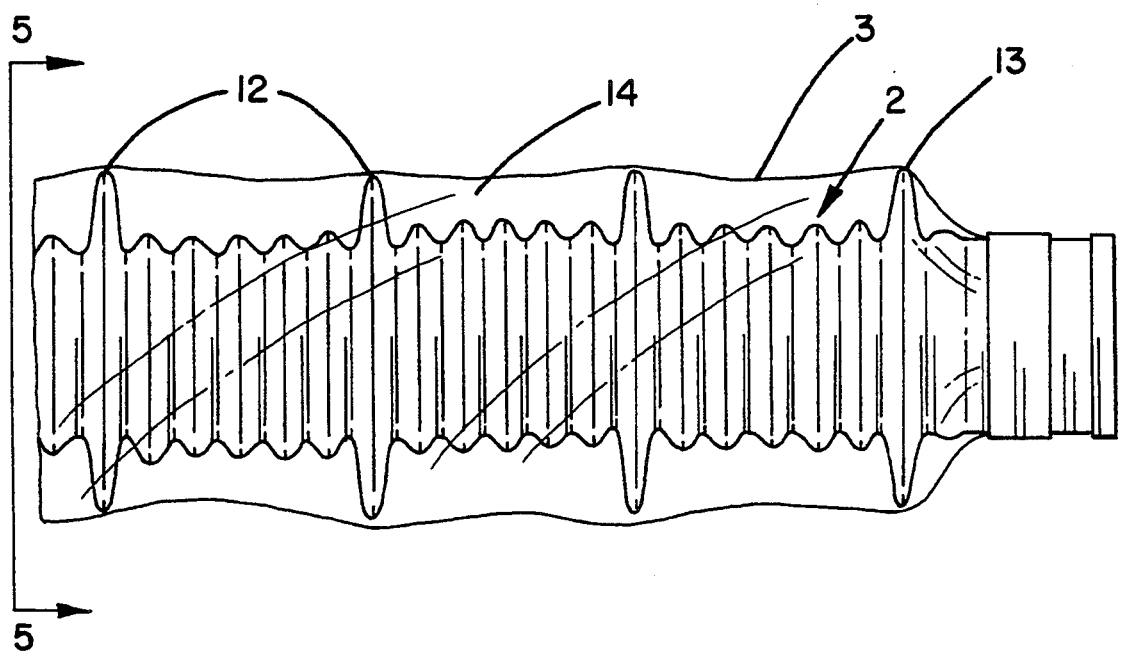
FIG. 4 is an illustration of another arrangement within the scope of the present invention.

FIG. 4 shows another embodiment of the insulated breathing tube assembly of FIG. 1 wherein intermittently spaced corrugations 12 are provided which have outer crests 13 that are substantially greater in height than the corrugations of the tube adjacent thereto. The consequence of providing such intermittently spaced larger corrugations is that it is assures that casing 3 will not contact corrugated tube 2 except at such intermittent corrugations. This arrangement has the effect of maximizing the distance between corrugated tube 2 and casing 3 and compartmentalize the dead air space between the corrugated tube and the casing. One such compartment is shown at 14 in FIG. 4. It should be noted however, that even in the embodiment of FIG. 4 casing 3 is sized to be loose fitting and not in taut contact with outer crests 13.

Figure 5:
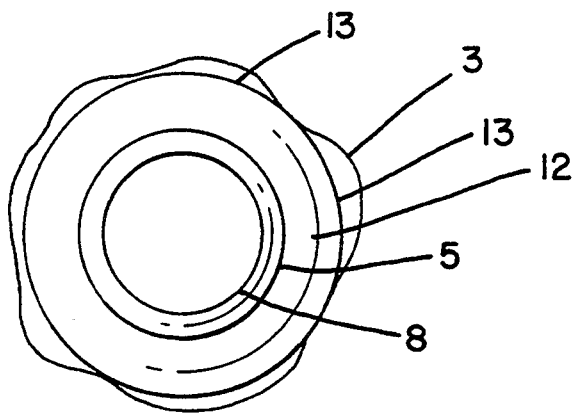
FIG. 5 is a cross sectional view taken along a plane passing through line 5—5 of FIG. 4.

FIG. 5 shows a cross section of the embodiment of FIG. 4 along a plane passing through line 5—5 of FIG. 4 showing intermittently spaced corrugations 12 and outer crests 13.

There are two important features of this invention which will now be more fully described. It is essential in the invention to have the outer casing 3 of a thickness which is less than the thickness of the inner corrugated tube 2. Further, the outer casing should be of an internal diameter which is greater than the external diameter of the corrugated tube 2. Most preferably the ratio of these diameters is 1 to 1.25 or greater, or expressed in absolute measurements the inner diameter of the casing 3 should be at least two centimeters greater than the external diameter of tube 2 and preferably more.

Figure 6:
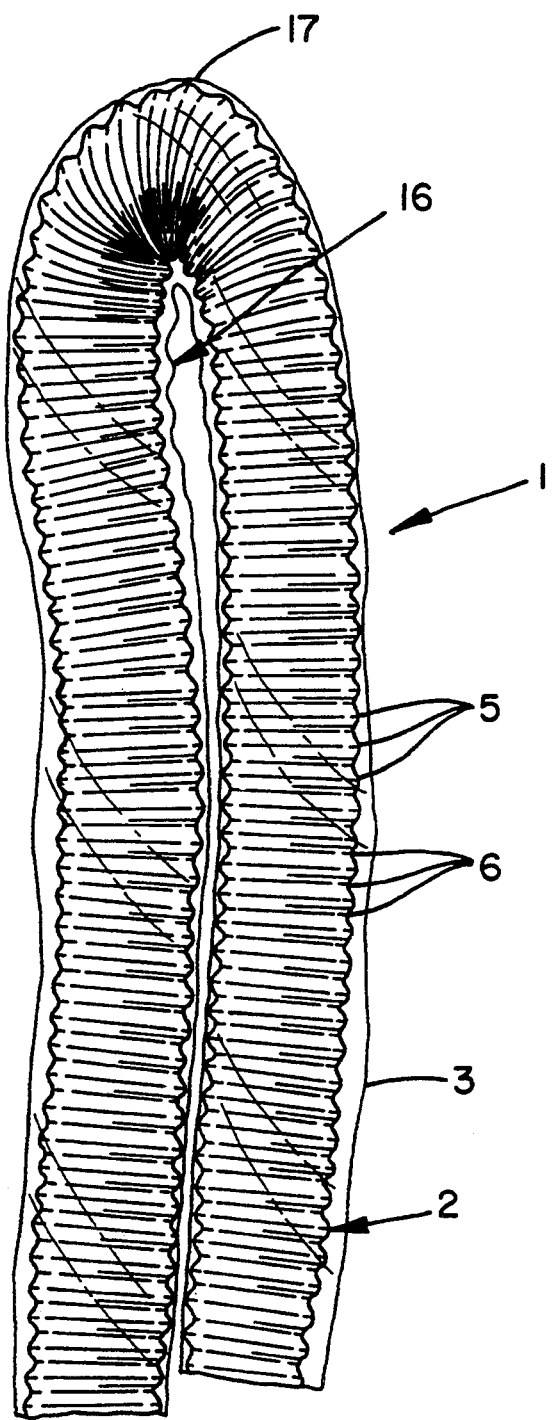
FIG. 6 is an illustration of the insulated breathing tube of this invention being folded back upon itself in hairpin fashion.

The reason for the greater diameter and thinner material is that frequently the breathing tubes are subject to being tightly kinked in hair-pin fashion during actual use. In essence the tube is virtually bent back upon itself as shown in FIG. 6 yet air flow through the tube must be maintained. A corrugated tube has been found to avoid kinking and shutting off the air flow but, nevertheless a thick outer casing will bunch on the inside of a hairpin bend at inner bend areas 16 and prevent such a bend from being formed or in the alternative cause even a corrugated tube to kink and shut off air flow. A thin casing avoids the problem of bunching of material on the inside of a hair pin bend and therefore should be selected for the casing material.

Generally both the materials of the casing as well as the corrugated tube should be a clear transparent polymeric resinous material. Examples of such material are polyproplene, polyetheylene, and copolymers, block polymers and blends of the same. Also suitably are polystyrene, polyvinyl acetate, polyvinyl choloride and other materials either alone or in blends with each other.

Such materials are well known in the art and are commonly referred to as plastics. Any such plastic or blend thereof can be useful if it can be made to be flexible, clear and non-reactive to the anesthesia gasses to which it would normally be subjected. Such plastics or blends thereof should also be inert to cleaning solutions and other chemicals and reagents commonly used in hospitals.

Another reason for having the outer casing diameter greater than the diameter of the corrugated tube is to optimize the dead air space created there between. Generally it has been found that selecting an outer casing which has a volume of seven cubic centimeters per centimeter encasing a corrugated tube having 3.5 cubic centimeters per centimeter is desirable. In essence then the linear volume of the insulating dead air space between the casing and the corrugated tube is equal to the linear volume of the corrugated tube itself. This has been found to be desirable in sizing the insulating dead air space.

Moreover, it is essential that when a breathing tube is subjected to a hairpin bend the outer casing should not interfere with the ability of the breathing tube to be so shaped. Consequently a larger diameter casing permits such bending, keeping in mind that the casing is affixed at both of its ends to the respective ends of the corrugated tube to form the dead air space.

In addition it has been found that when the casing and the corrugated tube are positioned with the casing ensleeving the corrugated tube and the respective ends of each of the corrugated tube and the casing are affixed or sealed to define the annular air space therebetween that the casing should be slightly longer than the corrugated tube and longitudinally compressed slightly so that when sealed to the corrugated tubes the ends are juxtaposed. In essence then the casing takes on a crinkled appearance. It has the appearance of a piece of paper that has been crumpled and then flattened. The benefit of having a casing which is not taut, but somewhat longer than the corrugated tube to which it is affixed it is that when the breathing tube is subjected to a hairpin bend the casing does not interfere with such bending especially on the outside portion of the hairpin bend as shown at 17 on FIG. 6 where the casing normally would become taut and prevent further bending of the corrugated tube without rupturing or breaking loose from the corrugated tubing at one of its ends.

Proper sizing of the length of the outer casing is determined by selecting a casing length such that when it is sealed to a corrugated tube which it ensleeves the breathing tube formed thereby can be doubled back upon itself forming a hairpin bend therein and the outer casing is just taut across the outside surfaces of the corrugated tube which it encases. As previously noted FIG. 6 is illustrative of a hairpin bend in a breathing tube and illustrates the casing contacting the corrugation crests 5 of the corrugated tube 2 on the outer side of the hair pin bend.

In actual practice the breathing tube of the present invention may be combined with a second such tube, one of which provides inhalant gasses to the patient and the other of which provides for the expulsion of exhalant gasses from the patient. Generally speaking the reason for the use of two tubes instead of a single coaxial tube is that the exhalant gasses most desirably are vented to a part of the respiratory system other than that to which the patient is connected. In this regard the two tubes are typically joined by a "Y" connector just prior to attaching them to the patient, for example, by an endotracheal catheter or face mask etc.

Another important feature of the present invention relates to the relative surface area of the corrugated tube relative to the surface area of the envelope when the tube is in its relaxed or unstretched state. The total surface area of the casing surrounding the tube is substantially less than the enclosed surface area of the breathing tube because of the additional surface area provided by the corrugations. In some instances the surface area of the corrugated tubing may be as much as four times the surface of the envelope which encloses the corrugated breathing tube. Since the benefits derived from the use of the envelope are related to the radiation loss and the convention loss of heat from the tube the relative surface areas are of importance.

It will be understood that the foregoing are but a few examples of arrangements within the scope of the present invention and that various other arrangements also within the scope of the present invention will occur to those skilled in the art upon reading the disclosure set forth hereinbefore.

Having thus described the invention what is claimed is:

1. An insulated breathing tube arrangement having an air impervious corrugated tube for carrying respiratory gases and an outer casing of first internal diameter for insulating the corrugated tube, said corrugated tube being located within said casing and having an outer diameter less than said internal diameter of said casing, said casing being of an overall length greater than the length of said corrugated tube and being sealed at its ends to the ends of the corrugated tube such that the casing is in a slightly longitudinally compressed state relative to said corrugated thereby defining an insulating dead air space between said corrugated tube and said casing, the volume of the dead air space between said corrugated tube and said casing per unit length being equal to the volume of the corrugated tube per unit of length, said casing further being of smooth sidewall construction and being of a thickness which is less than the thickness of said corrugated tube arrangement.

* * * * *